US009492337B2

(12) United States Patent
Ehrnsperger et al.

(10) Patent No.: US 9,492,337 B2
(45) Date of Patent: Nov. 15, 2016

(54) SUBSTRATE COMPRISING ONE OR MORE HUMAN MILK OLIGOSACCHARIDES AND DISPOSABLE ABSORBENT ARTICLE COMPRISING THE SUBSTRATE

(71) Applicant: The Procter & Gamble Company, Cincinnati, OH (US)

(72) Inventors: Bruno Johannes Ehrnsperger, Bad Soden (DE); Bernard Hanke, Bad Sahwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 504 days.

(21) Appl. No.: 13/868,225

(22) Filed: Apr. 23, 2013

(65) Prior Publication Data

US 2013/0281948 A1    Oct. 24, 2013

(30) Foreign Application Priority Data

Apr. 24, 2012  (EP) .................................... 12165272

(51) Int. Cl.
| A61F 13/15 | (2006.01) |
| A61F 13/20 | (2006.01) |
| A61F 13/84 | (2006.01) |
| A61L 15/44 | (2006.01) |
| A61L 15/46 | (2006.01) |
| A61L 15/60 | (2006.01) |

(52) U.S. Cl.
CPC ..... *A61F 13/8405* (2013.01); *A61F 13/15577* (2013.01); *A61L 15/44* (2013.01); *A61L 15/46* (2013.01); *A61L 15/60* (2013.01); *A61L 2300/232* (2013.01)

(58) Field of Classification Search
CPC combination set(s) only.
See application file for complete search history.

(56) References Cited

U.S. PATENT DOCUMENTS

| 3,860,003 | A |   | 1/1975  | Buell |
| 4,788,237 | A | * | 11/1988 | Le-Khac .................... 524/55 |
| 5,176,911 | A |   | 1/1993  | Tosi et al. |
| 5,221,274 | A |   | 6/1993  | Buell et al. |
| 5,480,643 | A |   | 1/1996  | Donovan et al. |
| 5,538,783 | A |   | 7/1996  | Hansen et al. |
| 5,554,145 | A |   | 9/1996  | Roe et al. |
| 5,569,234 | A |   | 10/1996 | Buell et al. |
| 5,580,411 | A |   | 12/1996 | Nease et al. |
| 5,607,760 | A |   | 3/1997  | Roe |
| 5,801,116 | A |   | 9/1998  | Cottrell et al. |
| 6,004,306 | A |   | 12/1999 | Robles et al. |

(Continued)

FOREIGN PATENT DOCUMENTS

| EP | 0 691 133 A |   | 12/1999 |            |
| EP | 2656862     | * | 10/2013 | A61L 15/28 |

(Continued)

OTHER PUBLICATIONS

Structural Basis for the Interaction Between Human Milk Oligosaccharides and the Bacterial Lectin Pa-IIL, of Pseudominas Aeroginosa, Biochem. J., vol. 389, 2005, pp. 325-332.

(Continued)

*Primary Examiner* — Michele M Kidwell
(74) *Attorney, Agent, or Firm* — William E. Gallagher; Andrew A Paul; Abbey Lopez

(57) ABSTRACT

The present disclosure relates to a substrate that includes one or more human milk oligosaccharides. A disposable absorbent article may include the substrate having one or more human milk oligosaccharides.

16 Claims, 1 Drawing Sheet

(56) References Cited

U.S. PATENT DOCUMENTS

| | | | |
|---|---|---|---|
| 6,716,435 B1 | 4/2004 | Farmer et al. | |
| 7,893,041 B2* | 2/2011 | Morrow et al. | 514/62 |
| 7,960,604 B2 | 6/2011 | Tengberg et al. | |
| 2007/0237834 A1* | 10/2007 | Gupta | 424/630 |

FOREIGN PATENT DOCUMENTS

| | | | | |
|---|---|---|---|---|
| WO | WO 00/69483 A1 | 11/2000 | | |
| WO | 2005/055944 | * 6/2005 | | |
| WO | WO 2007/136176 A1 | 11/2007 | | |
| WO | 2009/155665 | * 12/2009 | | A61K 31/7012 |
| WO | WO 2011/008087 A1 | 1/2011 | | |
| WO | 2012/076321 | * 5/2012 | | A61K 31/7012 |

OTHER PUBLICATIONS

International Search Report, PCT/US2013/037577, dated May 27, 2013, 10 pages.
Comparison of the Effect of Human Milk and Topical Hydrocortisone, Pediatric Dermatology, Jan. 5, 2013, 5 pgs.
Topical Use of Human Breast Milk for Diaper Rash in Infants, International Journal of Advanced Nursing Studies 1 (2) (2012) 98-108, 11 pgs.
DM Tampon with Probiotics Lactic Acid Producing Bacteria, 1 pg.
Infection and Immunity, Brassart, et al, 1991, 59(5): 1605-1613, 10 pgs.

* cited by examiner

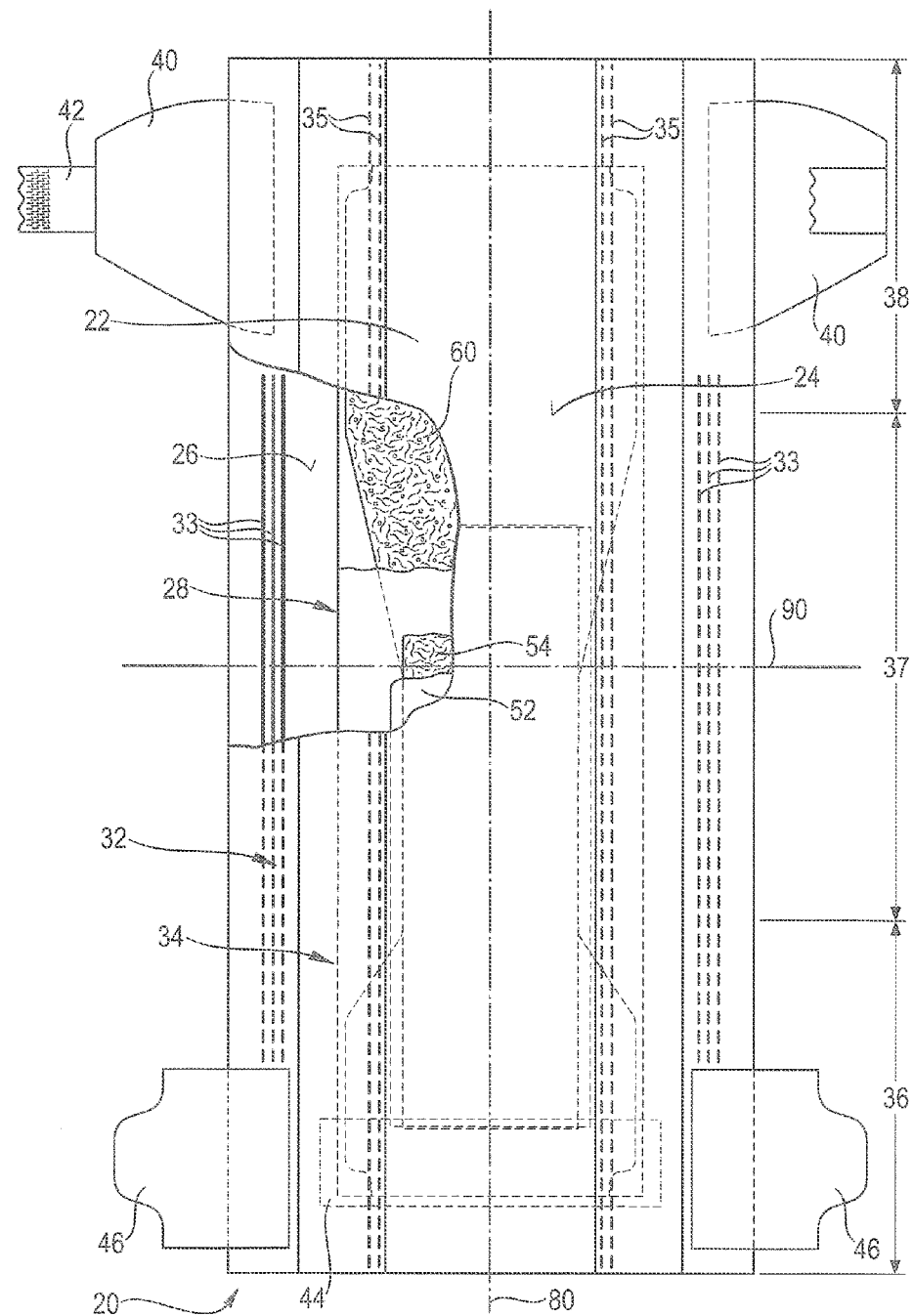

SUBSTRATE COMPRISING ONE OR MORE HUMAN MILK OLIGOSACCHARIDES AND DISPOSABLE ABSORBENT ARTICLE COMPRISING THE SUBSTRATE

CROSS REFERENCE TO RELATED APPLICATION

This application claims priority under 35 U.S.C. §119 to European Patent Application No. EP 12165272.0, filed Apr. 24, 2012, which is hereby incorporated by reference in its entirety.

FIELD OF THE INVENTION

The present disclosure relates to a substrate such as a nonwoven web, film, tissue, pulp and superabsorbent polymer, which comprises one or more human milk oligosaccharides. More particularly, the present disclosure provides a disposable absorbent article such as a diaper, a pant, an adult incontinence product, an absorbent insert for a diaper or pant, a wipe or a feminine hygiene product, such as a sanitary napkin and a panty liner and the like. The disposable absorbent article comprises the substrate having one or more human milk oligosaccharides. The present disclosure also provides a process for manufacturing a disposable absorbent article comprising the substrate.

BACKGROUND OF THE INVENTION

Many types of disposable absorbent articles, such as diapers, have a relatively high capacity for absorbing urine and other body exudates. Disposable absorbent articles of this type generally comprise a liquid-pervious topsheet, a liquid-impervious backsheet and an absorbent core comprised between the topsheet and the backsheet. Although these types of absorbent structures may be highly efficient for the absorption of liquids, it is well recognized that long-term wear of such structures may lead to skin which is compromised in terms of being over hydrated or exposed to skin irritants commonly found in body exudates. It is generally known that skin covered by disposable absorbent articles tends to be more susceptible to skin disorders, including diaper rash, erythema (i.e., redness), heat rash, abrasion, pressure marks and loss of skin barrier function.

Diaper rash is found on the skin of baby's diaper area. Most diaper rashes are caused by prolonged contact with the moisture, germs, enzymes, ammonia of the stool and urine. Some diaper rashes are caused by fungi infection ("The effect of antibacterial agent for *Candida albicans* inhibition of diaper rash", Palpu Chongi Gisul, Journal of Korea Technical Association of the Pulp and paper Industry, 33(3), p. 69-74). *Candida albicans* is one of the contributors to diaper rash.

To address the concerns of skin disorders associated with wearing absorbent articles, the caregiver often applies skin protective products such as Vaseline®, medicated ointments, powders, etc. to the buttocks, genitals, anal and/or other regions before placing the disposable absorbent article on the wearer. This procedure usually involves the caregiver applying the skin protective to their hands, and then wiping the same on the skin of the infant. To eliminate the need for this wasteful, messy and time-consuming procedure, there have been attempts to prepare absorbent articles which contain a protective or therapeutic skin care substance on the article's topsheet. By analogy, in applying skin protective products to the wearer's skin, before placing the disposable absorbent article on the wearer, wipes comprising such skin protective products may be used.

Probiotic agents generally are microorganisms that confer a benefit when they grow in a particular environment, by inhibiting the growth of other pathogenic microorganisms in the same environment. The nutritional use of probiotic bacteria, especially *Lactobacillus* and *Bifidobactierium* strains, that colonize the gut has been previously disclosed (Winberg et al., *Pediatr. Nephrol.* 7:509-514, 1993; Malin et al, *Ann. Nutr. Metab.* 40:137-145, 1996; and U.S. Pat. No. 5,176,911).

It has been discovered that probiotic acid-producing bacteria are effective in inhibiting, preventing and/or eliminating dermal/epithelial infections by preventing the growth of dermal pathogens which grow upon use of diapers and other sanitary products. Such probiotic acid-producing bacteria were included in disposable absorbent articles. In this way, they also promote a healthy skin flora. The healthy skin flora is able to suppress harmful pathogenic microorganisms and in this way maintain and promote a healthy skin.

Disposable feminine care products, such as tampons and sanitary napkins, impregnated with lactic acid producing bacteria can preserve a normal flora of microorganisms in the urogenital tract of women, and thereby preventing urogenital infections, or regenerating a normal flora of microorganisms in the urogenital tract of women.

However, these disposable absorbent articles require the addition of living microorganisms which may not be appealing to many consumers as it may be perceived as a risk of bacteria proliferation and potential infections.

There is still a need to provide a disposable absorbent article designed to deliver compositions to address skin disorders e.g., diaper rash, in order to maintain or improve skin health in regions of the wearer's body covered by disposable absorbent articles. Such disposable absorbent articles would not require intervention from the caregiver in the form of manual applications of skin care compositions.

SUMMARY OF THE INVENTION

It is an object of the present disclosure to provide a substrate selected from the group consisting of a nonwoven web, a film, a tissue, a pulp and a superabsorbent polymer wherein at least a portion of the substrate comprises one or more human milk oligosaccharides. The one or more human milk oligosaccharides comprise a linear or branched chain of carbohydrate units wherein the overall carbohydrate unit number is no more than 10, each carbohydrate unit containing 3 to 6 carbon atoms, wherein said carbohydrate units are covalently bound to each other directly or indirectly by an ether function.

More particularly, the present disclosure provides a disposable absorbent article which is selected from the group consisting of a diaper, a pant, an adult incontinence product, an absorbent insert for a diaper or pant, a wipe and a feminine hygiene product, such as a sanitary napkin and a panty liner, wherein one or more of the said substrates forms at least a portion of the disposable absorbent article.

The present disclosure also refers to a disposable absorbent article which is selected from the group consisting of a diaper, a pant, an adult incontinence product, an absorbent insert for a diaper or pant, and a feminine hygiene product, such as a sanitary napkin and a panty liner, the disposable absorbent article having a backsheet, a topsheet and an absorbent core disposed between the backsheet and the topsheet, wherein one or more of the said substrates forms at least a portion of the disposable absorbent article.

The present disclosure also provides a process for manufacturing a disposable absorbent article comprising the substrate. The process comprises the step of applying an amount of one or more human milk oligosaccharides to the substrate, via spraying, printing, coating, slot coating, extrusion, microencapsulation or any combination thereof.

BRIEF DESCRIPTION OF THE DRAWINGS

While the specification concludes with claims particularly pointing out and distinctly claiming the present disclosure, it is believed that the same will be better understood from the following description read in conjunction with the accompanying drawings in which:

FIG. 1 shows a diaper as an exemplary embodiment of an absorbent article;

DETAILED DESCRIPTION OF THE INVENTION

Definition of Terms

The term "absorbent article" as used herein refers to devices which absorb and contains body exudates, and, more specifically, refers to devices which are placed against or in proximity to the body of the wearer to absorb and contain the various exudates discharged from the body.

Typical absorbent articles of the present disclosure include but are not limited to diapers, adult incontinence briefs, training pants, diaper holders and liners, absorbent inserts and the like, as well as feminine hygiene products, such as sanitary napkins and panty liners, and the like. Absorbent articles also include wipes, such as household cleaning wipes, baby wipes, and the like.

The term "absorbent insert" and "insert" as used herein refer to a component of a wearable absorbent article that is adapted to contain and/or absorb urine, feces, menses or any combination thereof, and is adapted to be installable and removable as a modular unit, from an outer cover or chassis of a diaper, a pant or diaper holder.

The term "acquisition system" as used herein is a layer that serves several functions including receiving a surge of liquid, such as a gush of urine and serving as a temporary reservoir for the fluid until the absorbent core can absorb the liquid. The acquisition system can efficiently transport fluids over the surface of the absorbent core and also into the absorbent core, and drain substantially completely into the absorbent core in order to remain receptive for subsequent fluid loadings.

The term "adult incontinence product" as used herein refers to an adult diaper made to be worn by an adult person with a body generally larger than that of an infant or toddler. Diapers become necessary for adults with various conditions, such as incontinence, mobility impairment, or dementia. Adult incontinence products are made in various forms, including those resembling traditional child diapers, underpants, and pads resembling sanitary napkins (incontinence pads).

"Comprise," "comprising," and "comprises" as used herein are open ended terms, each specifying the presence of what follows, e.g., a component, but not precluding the presence of other features, e.g., elements, steps or components known in the art, or disclosed herein.

The term "diaper" as used herein refers to an absorbent article that is intended to be worn by a wearer about the lower torso to absorb and contain exudates discharged from the body. Diapers may be worn by infants (e.g., babies or toddlers) or adults. They may be provided with fastening elements.

"Disposable" as used herein refers to describe absorbent articles which generally are not intended to be laundered or otherwise restored or reused (i.e., they are intended to be discarded after a single use and, may, to be recycled, composted or otherwise discarded in an environmentally compatible manner).

"Feminine hygiene product" as used herein refers to a personal care product used by women during menstruation, vaginal discharge, and other bodily functions related to the vulva. Feminine hygiene product may include sanitary napkins or towels, panty liners, tampons, menstrual cups, and feminine wipes.

The term "film" as used herein refers to a substantially non-fibrous sheet-like material wherein the length and width of the material far exceed the thickness of the material. Typically, films have a thickness of about 0.5 mm or less. Films used in disposable absorbent articles may be configured to be liquid impermeable and/or vapor permeable (i.e., breathable).

The term "formulation" as used herein refers to a composition that comprises one or more human milk oligosaccharides and further comprises additional ingredients mixed together according to a formula. For the present disclosure, suitable formulations include emulsions, creams, ointments, salves, powders, suspensions, solutions, encapsulations, gels and combinations thereof.

The term "human milk oligosaccharide" as used herein refers to a linear or branched chain of carbohydrate units wherein the overall carbohydrate unit number is from 2 to no more than 32. Each carbohydrate unit containing 3 to 6 carbon atoms, wherein said carbohydrate units are covalently bound to each other directly or indirectly by an ether function. 5 monosaccharides may be used as a carbohydrate unit to form a human milk oligosaccharide: D-glucose, D-galactose, L-fucose, N-acetylglucosamine, and N-acetylneuraminic acid ("sialic acid").

The term "immobilizing agent" as used herein refers to an agent capable of immobilizing the composition in the desired location in or on the substrate. The immobilizing agent counteracts the tendency of the composition to migrate or flow by keeping the composition primarily localized on the surface or in the region of the substrate to which the composition is applied.

The term "microorganism" as used herein refers to a microscopic organism that comprises either a single cell (unicellular), cell clusters, or no cell at all (acellular). Microorganism includes bacteria, fungi, archaea, and protists; microscopic plants (green algae); and animals such as plankton and the planarian. Microorganism also includes viruses.

The term "nonwoven web" as used herein refers to a manufactured material, web, sheet or batt of directionally or randomly oriented fibers, bonded by friction, and/or cohesion and/or adhesion, excluding paper and products which are woven, knitted, tufted, stitch-bonded, incorporating binding yarns or filaments, or felted by wet milling, whether or not additionally needled. The fibers may be of natural or man-made origin. The fibers may be staple or continuous filaments or be formed in situ. The porous, fibrous structure of a nonwoven may be configured to be liquid permeable or impermeable, as desired.

The term "pant" as used herein refers to a disposable absorbent article having fixed edges, a waist opening and leg openings designed for infant or adult wearers. A pant-type disposable absorbent article is placed in position on the wearer by inserting the wearer's legs into the leg openings and sliding the pant-type disposable absorbent article into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the term "pant" or "pants" are used herein, pants are also commonly referred to as "closed diapers", "prefastened diapers", "pull-on diapers", "training pants" and "diaper-pants".

The term "pulp" as used herein refers to a fiber obtained from a tree or plant. Comminuted wood pulp is generally referred to as absorbent cellulose fibers or as airfelt, creped cellulose wadding, including co-form, chemically stiffened, modified or cross-linked cellulosic fibers as well as mechanical and semi-chemical pulps including for example, groundwood, thermomechanical pulp, chemi-mechanical pulp (CMP), chemi-thermomechanical pulp (CTMP), neutral semi-chemical sulfite pulp (NSCS).

The term "substrate" as used herein refers to a material suitable for use in a disposable absorbent article. When used in a disposable absorbent article, the substrate may be comprised by, or forming, or used for manufacturing of the topsheet and/or the absorbent core and/or the acquisition system and/or the leg cuffs and/or the barrier cuffs and/or the side flaps and/or the side panels and/or the wings of an absorbent article. Suitable materials include nonwoven webs, films, tissue, pulp, superabsorbent polymer or combinations thereof.

The term "Superabsorbent polymer" as used refers to substantially water-insoluble polymer (particle) that can absorb at least 5 times their weight of an aqueous 0.9% saline solution by way of an osmotic mechanism. Obviously, it will absorb other aqueous liquids as well, such as urine and blood.

The term "Superabsorbent particulate polymer" as used herein refers to a superabsorbent polymer which is in particulate form so as to be flowable in the dry state.

The term "Superabsorbent foam" as used herein refers to a superabsorbent polymer which has a structure which results when a relatively monomer-free gas or relatively monomer-free liquid is dispersed as bubbles in a liquid containing polymerizable, superabsorbent-polymer-forming reactants, followed by expansion of the bubbles and polymerization of the reactants in the liquid which surrounds the expanded bubbles. The resultant polymerized, expanded structure can be in the form of a porous solidified structure which is an aggregate of cells, the boundaries or walls of which cells comprise solid superabsorbent polymers.

The term "tissue" as used herein refers to sheets of paper made by a process which may comprise the steps of forming an aqueous papermaking furnish, depositing this furnish on a foraminous surface, such as a Fourdrinier wire, and removing the water from the furnish (e.g., by gravity or vacuum-assisted drainage), forming an embryonic web, transferring the embryonic web from the forming surface to a transfer surface. The web is then transferred to a fabric upon which it is through air dried to a final dryness after which it is wound upon a reel.

The term "web" means a material capable of being wound into a roll. Webs may be nonwovens.

The term "wipe" as used herein refers to a piece of material, generally nonwoven material, used to cleanse body parts. For the present disclosure, wipe articles are used for the cleaning of the peri-anal area after defecation or for the cleansing of other body parts after a change of absorbent article.

Incorporation of One or more Human Milk Oligosaccharides in a Disposable Absorbent Article The inventors have now found that the addition of one or more human milk oligosaccharides in a disposable absorbent article may help to promote a healthy skin flora.

One or more human milk oligosaccharides may act either by attachment to the receptors of harmful pathogenic microorganisms and render these microorganisms harmless or as prebiotics agents for healthy skin flora able to suppress the harmful pathogenic microorganisms such as *Candida albicans*.

As a result, the disposable absorbent article comprising one or more human milk oligosaccharides may maintain or improve the skin health of the wearer in order to address the concerns of skin disorders such as diaper rash associated with wearing disposable absorbent articles.

It is intended that the use of the disposable absorbent article may deliver an amount of one or more human milk oligosaccharides to the wearer's skin in order to maintain or improve the skin health.

The human milk is a rich source of complex human milk oligosaccharides synthesized within the mammary gland. The human milk contains more than 150 different oligosaccharides (Genetic expression and nutrition, 2003, 50, p. 138-152).

It is known that these human milk oligosaccharides can attach to the receptors of harmful pathogenic microorganisms and render these microorganisms harmless. The adhesion of these pathogenic microorganisms to their target cells is inhibited. However, hitherto, the human milk oligosaccharides have only been purposefully added to nutritioning.

For instance, a way to improve the intestinal flora of bottle-fed babies is to selectively stimulate the *bifidobacteria* already present in the bottle-fed infant's intestine by specific non-digestible oligosaccharides, i.e. prebiotics. Prebiotics agents generally are defined as non-digestible food ingredients that selectively stimulate the growth and/or activity of one or more bacteria, for instance in the colon and thereby beneficially affect the host (Gibson and Roberfroid, *J. Nutr.* 125:1401-14121995). The prebiotic agents cannot be digested by harmful pathogenic microorganisms, but they act as food for probiotic (lactic acid producing) bacteria such as *Lactobacillus* and *Bifidobactierium* strains. Also, mixtures of oligosaccharides and polysaccharides have been proposed as prebiotics, e.g., in International Application No. WO 00/08948. One example is the combination of galacto-oligosaccharide with fructopolysaccharides. The bifidobacteria level in infants receiving a formula containing these prebiotics has been shown to be elevated in comparison with a standard formula (see e.g., Moro et. al. J. Pediatr. Gastroenterol. Nutr. 34:291-295, 2002).

It may have been presumed that including one or more human milk oligosaccharides into a disposable absorbent article may interfere with the performance of the disposable absorbent articles such as the absorption capacity. However, surprisingly, the inventors have found that the addition of one or more human milk oligosaccharides in a disposable absorbent article has little to no impact on the technical performance of the final product.

The Substrate

A wide variety of materials can be used as the substrate. When the substrate is a nonwoven web, film or tissue, the following nonlimiting characteristics are desirable: (i) sufficient wet strength for use, (ii) sufficient softness, (iii) sufficient thickness, (iv) appropriate size, (v) air permeability, and (vi) hydrophilicity.

In the present disclosure, the substrate is selected from a group consisting of nonwoven web, film, tissue, pulp and superabsorbent polymer. The substrate may also include laminates comprising two or more layers of such materials.

When the substrate is a nonwoven web, film or tissue, the substrate may have a basis weight from 5 to 200 g/m². When the substrate is comprised by, or forms the topsheet, the core cover, the legs cuffs and/or the barrier cuffs and/or the side flaps and/or the wings of a disposable absorbent article such as, it may have for example a basis weight from 5 to 200 g/m², or from 8 to 40 g/m², or from 8 to 30 g/m². When the substrate is used as, or in a wipe, it may for example have a basis weight from 15 to 100 g/m², or from 30 to 95 g/m², or from 40 to 85 g/m², or from 45 to 75 g/m².

When the disposable absorbent article includes a layer comprising pulp and/or superabsorbent polymer as the substrate(s), the basis weight of this layer may be from 50 to 800 g/m², or from 100 to 600 g/m², or from 200 to 400 g/m².

1) Nonwoven

An example of a suitable substrate which meets the above criteria is a nonwoven web.

Exemplary configurations employ nonwoven webs since they are economical and readily available in a variety of materials. By "nonwoven", it is meant that the layer is comprised of fibers which are not woven into a fabric but rather are formed into a web, sheet, mat, or pad layer.

The nonwoven web may comprise fibers made by nature (natural fibers), made by man (synthetic or man-made), or combinations thereof. Example natural fibers include but are not limited to: animal fibers such as wool, silk, fur, and hair; vegetable fibers such as cellulose, cotton, flax, linen, and hemp; and certain naturally occurring mineral fibers.

Synthetic fibers can be derived from natural fibers or not. Example synthetic fibers which are derived from natural fibers include but are not limited to rayon and lyocell, both of which are derived from cellulose, a natural polysaccharide fiber. Synthetic fibers which are not derived from natural fibers can be derived from other natural sources or from mineral sources. Example synthetic fibers derived from natural sources include but are not limited to polysaccharides such as starch. Example fibers from mineral sources include but are not limited to polyolefin fibers such as polypropylene and polyethylene fibers, which are derived from petroleum.

Common synthetic fiber include but are not limited to nylon (polyamide), acrylic (polyacrylonitrile), aramid (aromatic polyamide), polyolefin (polyethylene and polypropylene), polyester, butadiene-styrene block copolymers, natural rubber, latex, and spandex (polyurethane).

2) Film

The substrate can be a film.

A film may comprise any known material being moisture pervious, liquid pervious or liquid impervious. For example, a film comprised by the topsheet is rather liquid pervious. An impervious film may be rendered pervious by being microporous or apertured.

3) Tissue

The present disclosure is applicable to tissue paper in general, including but not limited to conventionally felt-pressed tissue paper; pattern densified tissue paper such as exemplified by Sanford-Sisson (U.S. Pat. No. 3,301,746) and its progeny; and high-bulk, uncompacted tissue paper such as exemplified by Salvucci (U.S. Pat. No. 3,812,000). The tissue paper may be of a homogenous or multilayered construction; and tissue paper products made therefrom may be of a single-ply or multi-ply construction. The tissue paper may have a basis weight of between 10 g/m² and 80 g/m², and density between 0.1 g/cm³ and 1.0 g/cm³. The basis weight may not be below 35 g/m²; and the density will be below 0.8 g/cm³. The density may be between 0.2 g/cm³ and 0.8 g/cm³.

One or more human milk oligosaccharides of the present disclosure can also be applied to uncreped tissue paper. Uncreped tissue paper, as used herein, refers to tissue paper which is non-compressively dried, such as through air drying. Resultant through air dried webs are pattern densified such that zones of relatively high density are dispersed within a high bulk field, including pattern densified tissue wherein zones of relatively high density are continuous and the high bulk field is discrete.

4) Cellulose Fiber and Pulp

Cellulosic Fiber

In general, a cellulosic fiber is selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber, bleached softwood sulfite pulp fiber, unbleached softwood sulfite pulp fiber, cotton linters, mercerized dissolving pulp fiber, unmercerized dissolving pulp fiber, and mixtures thereof.

Mechanical Pulp Fibers

As used herein, the term "mechanical pulp fibers" shall mean pulp fibers derived from wood which retain a substantial portion of the lignin present in the unpulped wood. In some exemplary configurations, greater than about 80% yield based upon the weight of the unpulped wood may be retained. One type of mechanical pulp fibers which can be used is known in the art as thermomechanical pulp (TMP). Another type of mechanical pulp fibers for use in conjunction with the present disclosure are chemithermomechanical pulp (CTMP) fibers, also sometimes referred to as chemically-modified thermomechanical pulp fibers.

5) Superabsorbent Polymer

The superabsorbent polymer herein is capable of absorbing liquids such as urine or blood and it swells thereby, often forming a gel. The superabsorbent polymer herein comprises superabsorbent particles or foams and may also comprise other components, such as fillers, flowing aids, process aids, anti-caking agents, odour control agents, colouring agents, etc.

The superabsorbent polymer is generally solid; this includes granules, beads, flakes, fibres, powders, platelets, spheres and other forms known in the art for superabsorbent polymers described herein.

In some exemplary configurations, the superabsorbent polymer is in the form of particles having a mass median particle size between 10 μm and 2 mm, or between 50 microns and 1 mm, or between 100 μm and 800 μm, as can for example be measured by the method set out in for example European Patent No. EP-A-0691133.

The superabsorbent polymers may comprise particles that are essentially spherical.

6) General Characteristics of the Substrate

When the substrate is a nonwoven web, film or tissue, it is typically designed to fit the area of the skin to which topical application is desired. In that case, the substrate is flexible enough such that, when impregnated with one or more human milk oligosaccharides, it readily fits along the skin, yet is strong enough so that it does not easily tear or crumble upon use. The water-insoluble substrate may be made solely of hydrophilic material, or made of a mixture of hydrophilic material and hydrophobic material, depending on its function. For instance, when the substrate forms a portion of the topsheet, the substrate may be rendered hydrophilic in order to allow the exudates discharged from the wearer to penetrate the topsheet through the absorbent core.

The substrate may not comprise an efficient amount of microorganisms in order to not be perceived as a risk of bacteria proliferation and potential infections.

The efficient amount of microorganisms may be more than 9 CFU (Colon Forming Units) per 0.1 square meter of a substrate. CFU as used herein means Colon Forming Units as determined with the Miles and Misra method (Miles, A A; Misra, S S, Irwin, J O (1938 November), "The estimation of the bactericidal power of the blood", *The Journal of hygiene* 38 (6), 732-49.

One Or More Human Milk Oligosaccharides

1) The Human Milk Oligosaccharides

Human milk is a rich source of complex oligosaccharides synthesized within the mammary gland. The concentration of this fraction varies widely with lactational stage, decreasing from large amounts of up to 50 g/l or more in colostrums to an average of 5 to 10 g/l in mature milk.

There are 150-200 different human milk oligosaccharides. Table 1, incorporated from Genetic and Nutrition, 2003, vol. 50, summarizes the compositions on oligosaccharides in term and preterm milk in relation to their structure.

TABLE 1

Major oligosaccharides in preterm and term human milk

| Trivial name | Abbreviation | Structure |
|---|---|---|
| Lactose | Lac | Gal$\beta$1-4Glc |
| 2N-Fucosyl-lactose[a] | 2N-Fuc-Lac | Fuc$\alpha$1-2Gal$\beta$1-4Glc |
| 3-Fucosyl-lactose | 3-Fuc-Lac | Gal$\beta$1-4Glc<br>3<br>$\square$<br>1<br>Fuc$\alpha$ |
| Lacto-N-tetraose (type 1) | LNT | Gal$\beta$1-3GlcNAc$\beta$1-3Gal$\beta$1-4Glc |
| Lacto-N-neo-tetraose (type 2) | neo-LNT | Gal$\beta$1-4GlcNAc$\beta$1-3Gal$\beta$1-4Glc |
| Lacto-N-fucopentaose I[a] | LNFP I | Fuc$\alpha$1-2Gal$\beta$1-3GlcNAc$\beta$1-3Gal$\beta$1-4Glc |
| Lacto-N-fucopentaose II[b] | LNFP III | Gal$\beta$1-3GlcNAc$\beta$1-3Galc$\beta$1-4Glc<br>4<br>$\square$<br>1<br>Fuc$\alpha$ |
| Lacto-N-fucopentaose III | LNFP III | Gal$\beta$1-4GlcNAc$\beta$1-3Gal$\beta$1-4Glc<br>3<br>$\square$<br>1<br>Fuc$\alpha$ |
| Lacto-N-fucopentaose V | LNFP V | Gal$\beta$1-3GlcNAc$\beta$1-3Gal$\beta$1-4Glc<br>3<br>$\square$<br>1<br>Fuc$\alpha$ |
| Lacto-N-difuco-hexaose I[c] | LNDFH I | Fuc$\alpha$1-2Gal$\beta$1-3GlcNAc$\beta$1-3Gal$\beta$1-4Glc<br>4<br>$\square$<br>1<br>Fuc$\alpha$ |
| Lacto-N-difuco-hexaose II | LNDFH II | Gal$\beta$1-3GlcNAc$\beta$1-3Gal$\beta$1-4Glc<br>4  3<br>$\square$  $\square$<br>1  1<br>Fuc$\alpha$  Fuc$\alpha$ |
| Sialy$\alpha$2-3lactose | NeuAc$\alpha$2-3Lac | NeuAc$\alpha$2-3Gal$\beta$1-4Glc |
| Sialy$\alpha$2-6lactose | NeuAc$\alpha$2-6Lac | NeuAc$\alpha$2-6Gal$\beta$1-4Glc |
| Sialyl-lacto-N-tetraose a (LST a) | NeuAc-LNT | NeuAc$\alpha$2-3Gal$\beta$1-3GlcNAc$\alpha$$\beta$1-3Gal$\beta$1-4Glc |
| Sialyl-lacto-N-tetraose b (LST b) | NeuAc-LNT | Gal$\beta$1-3GlcNAc$\beta$1-3Gal$\beta$1-4Glc<br>6<br>$\square$<br>2<br>NeuAc$\alpha$ |
| Sialyl-lacto-N-tetraose c (LST c) | NeuAc-LNT | NeuAc$\alpha$2-6Gal$\beta$1-4GlcNAc$\beta$1-3Gal$\beta$1-4Glc |
| Disialyl-lacto-N-tetraose | NeuAc$_2$LNT | NeuAc$\alpha$2-3Gal$\beta$1-3GlcNAc$\beta$1-3Gal$\beta$1-4Glc<br>6<br>$\square$<br>2<br>NeuAc$\alpha$ |

[a]Milk of women with secretor status.
[b]Le[a]-active components.
[c]Le[b]-active components.

Human milk oligosaccharides are composed of both neutral and anionic species with carbohydrate units having about 5 monosaccharides: D-glucose, D-galactose, L-fucose, N-acetylglucosamine, and N-acetylneuraminic acid ("sialic acid"). The basic structure of human milk oligosaccharides includes a lactose core (lactose is a disaccharide of glucose and galactose) at the reducing end which are elongated by N-acetyllactosamine units, with greater structural diversity provided by extensive fucosylation and/or sialylation wherein fucose and sialic acid residues are added at the terminal positions. Table 2 summarizes the structure of human milk oligosaccharides.

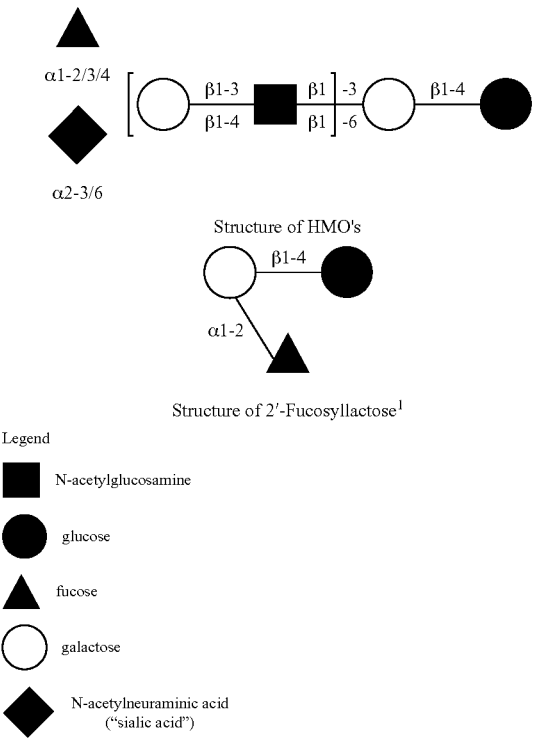

SCHEME 1. Schematic structure of human milk oligosaccharide

Structure of HMO's

Structure of 2'-Fucosyllactose[1]

Legend

■ N-acetylglucosamine

● glucose

▲ fucose

○ galactose

◆ N-acetylneuraminic acid ("sialic acid")

[1] http://web.me.com/lars_bode/bode-lab/Whatare_HMO.html

Human milk contains about 2.5 g/L of 2'-fucosyllactose. Thereby, this 2'-fucosyllactose is the most frequent human milk oligosaccharide. Major components are mono and difucosyllactose, lacto-N-tetraose (mainly type 1) and their mono- and difucosylated derivatives, as well as lacto-N-fucopentaose I and II and fucosylated lacto-N-hexaoses and lacto-N-octaoses.

Oligosaccharides in human milk are said to have a direct inhibitory effect on certain virulent abilities of pathogenic microorganisms acting in the intestinal area. Such microorganisms responsible for instance, for infectionous diseases such as diarrhea, adhere to the mucosal surface of their host. This type of adhesion is a receptor-mediated interaction between structures on the bacterial surface and complementary ligands on the mucosal surface of the host.

In order to prevent diaper rash, for which *Candida albicans* is one of the presumed pathogenic microorganisms, one or more human milk oligosaccharides can be added to a substrate. The substrate may form at least a portion of a disposable absorbent article.

One or more human milk oligosaccharides can then be delivered on the skin of the wearer during the use of the disposable absorbent article. The variety of oligosaccharides in the human milk may prevent the attachment of microorganisms such as *Candida albicans* by acting as analogs competing with the receptors onto the skin for *Candida albicans* binding. One or more human milk oligosaccharides comprised in a disposable absorbent article maintain a healthy skin flora.

2) Formulations

One or more human milk oligosaccharides may help to provide a protective function to address skin disorders e.g., diaper rash, or to maintain the wearer's skin healthy.

One or more human milk oligosaccharides might be delivered, either directly or indirectly to the skin of the wearer. One or more human milk oligosaccharides may maintain or improve the skin conditions in regions of the wearer's body covered by disposable absorbent articles.

One or more human milk oligosaccharides may be comprised in a variety of formulations, including, but not limited to, solutions with one or more solvents or one or more cosolvents, emulsions, lotions, creams, ointments, salves, powders, suspensions, encapsulations, gels, and the like. The formulations may remain on the substrate or may be eliminated afterwards, e.g., by evaporating the solvent such as water after one or more human milk oligosaccharides comprised in such formulation, has been applied onto the substrate.

Particularly, when the substrate is a nonwoven web, a film or a tissue, one or more human milk oligosaccharides may be comprised in a formulation.

To enhance immobility in or on the substrate of the formulations in which one or more human milk oligosaccharides may be comprised, the viscosity of the formulations such as a lotion should be as high as possible to prevent flow within the disposable absorbent article to undesired location.

Suitable viscosities for the formulations will typically range from about 5 to about 500 mPa·s, from about 5 to about 300 mPa·s, from about 5 to about 100 mPa·s, measured at 60° C. using a rotational viscometer (a suitable viscometer is available from Lab Line Instruments, Inc. of Melrose Park, Ill. as Model 4537). The viscometer is operated at 60 rpm using a number 2 spindle.

The inventors have also found that an immobilizing agent may counteract the tendency of the human milk oligosaccharides comprised in a formulation to migrate or flow by keeping the human milk oligosaccharides primarily localized on the surface or in the region of the article to which the formulation has been applied (e.g., due to urination). This is believed to be due, in part, to the fact that the immobilizing agent may raise the viscosity of the formulation.

For instance, types of ingredients that can be used as immobilizing agents, either alone, or in combination include waxes such as carnauba, ozokerite, beeswax, candelilla, paraffin, ceresin, esparto, ouricuri, rezowax, isoparaffin, and other known mined and mineral waxes. The high melt point of these materials can help immobilize the human milk oligosaccharides on the desired surface or location on the disposable absorbent article. Additionally, microcrystalline waxes are effective immobilizing agents. In some exemplary configurations, the wax may be a paraffin wax. In some exemplary configurations, the immobilizing agent is a paraffin wax such as Parrafin S. P. 434 from Strahl and Pitsch Inc. P.O. Box 1098 West Babylon, N.Y. 11704.

The formulations may include other components typically present in emulsions, creams, ointment, powders, suspensions, etc. of this type.

In order to better enhance the benefits to the wearer, additional ingredients can be included in the formulations such as a lotion. For example, the classes of ingredients that may be used and their corresponding benefits include, without limitation: solvents, skin protectants or emollients, viscosity modifiers, antifoaming agents (reduce the tendency of foaming during processing); antimicrobial actives; antifungal actives; antiseptic actives; antioxidants (product integrity); astringents—cosmetic; astringent—drug (a drug product which checks oozing, discharge, or bleeding when applied to skin or mucous membrane and works by coagulating protein); biological additives (enhance the performance or consumer appeal of the product); vitamins, colorants (impart color to the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors); fragrances (consumer appeal); humectants (increase the water content of the top layers of the skin); natural moisturizing agents (NMF) and other skin moisturizing ingredients known in the art; opacifiers (reduce the clarity or transparent appearance of the product); skin conditioning agents.

Stabilizers may be also added to enhance the shelf life of the formulations such as cellulose derivatives, proteins and lecithin.

All of these materials are well known in the art as additives for such formulations and may be employed in appropriate amounts.

A preservative may also be needed. Suitable preservatives include propyl paraben, methyl paraben, benzyl alcohol, benzylkonnium, tribasic calcium phosphate, BHT, or acids such as citric, tartaric, maleic, lactic, malic, benzoic, salicylic, and the like. Suitable viscosity increasing agents may include some of the agents described as effective immobilizing agents. Other suitable viscosity increasing agents may include alkyl galactomannan, silica, talc, magnesium silicate, sorbitol, colloidal silicone dioxide, magnesium aluminum silicate, zinc stearate, wool wax alcohol, sorbiton, sesquioleate, cetyl hydroxy ethyl cellulose and other modified celluloses. Suitable solvents may include propylene glycol, glycerine, cyclomethicone, polyethylene glycols, hexylene glycol, diol and multi-hydroxy based solvents. Suitable vitamins include A, D-3, E, B-5 and E acetate.

3) One or More Human Milk Oligosaccharides are Comprised in or on the Substrate

At least, a portion of a substrate comprises one or more human milk oligosaccharides.

Each human milk oligosaccharide comprises a linear or branched chain of carbohydrate units wherein the overall carbohydrate unit number is from 2 to no more than 32. Each carbohydrate unit contains 3 to 6 carbon atoms, wherein said carbohydrate units are covalently bound to each other directly or indirectly by an ether function.

One or more human milk oligosaccharides are selected from the group consisting of: lactose, 2'-fucosyllactose, 3'-fucosyllactose, difucosyllactose, lacto-N-tetraose (type 1), lacto-N-neo-tetraose (type 2), lacto-N-fucopentaoses I, II, III, IV and V, lacto-N-fucohexaose I, lacto-N-hexaose, lacto-N-neohexaose, fucosyllacto-N-hexaose I and IV, fucosyllacto-N-neohexaose, lacto-N-difuco-hexaoses I and II, lacto-N-octaoses, sialyα2-3lactose, sialyα2-6lactose, sialyl-lacto-N-tetraose a, b and c, and disialyl-lacto-N-tetraose, as illustrated in Table 1. These compounds are the major components of preterm and term human milk.

More particularly, one or more human milk oligosaccharides are selected from the group consisting of:

a human milk oligosaccharide wherein the human milk oligosaccharide comprises fucose-α(1→2)galalactose_β as a disaccharide unit, 2'-fucosyllactose, 3'-fucosyllactose, lacto-N-difuco-tetraose, lacto-N-difuco-hexose I, lacto-N-difuco-hexose II, lacto-N-fucopentaose I, lacto-N-fucopentaose II, lacto-N-fucopentaose III, and lacto-N-fucopentaose V, or mixtures thereof.

In or on the substrate, one or more human milk oligosaccharides may be comprised in a formulation. When applied to the substrate such as a nonwoven web, film or tissue, comprised by a disposable absorbent article, one or more human milk oligosaccharides in the formulation may be transferable to the wearer's skin by normal contact, wearer motion (thus creating friction), urine and/or body heat.

When applied to a substrate used in, or as a wipe, one or more human milk oligosaccharides in the formulation may be also readily transferable from the substrate to the skin by applying a relatively low force to the substrate (e.g., wiping a surface such as the skin in the perianal area with the wipe or rubbing the skin in the perianal area with the product applying surface).

The amount of transfer or migration of one or more human milk oligosaccharides onto the skin may depend on the amount of one or more human milk oligosaccharides being on the substrate. The amount of one or more human milk oligosaccharides from the formulation that may transfer or migrate to the wearer's skin may depend on factors such as the type of formulation that is applied, the portion of the body facing surface of the substrate where the formulation is applied, and the type of disposable absorbent article used to administer the formulation as well as the temperature of the skin and the movements of the wearer.

When the substrate is included in a layer underneath the topsheet, one or more human milk oligosaccharides may also be transferred to the wearer's skin. After discharge of the exudates and prior to their irreversible lock in the superabsorbent polymer, one or more human milk oligosaccharides may be dissolved in the urine and may flow back to the body-surface of the wearer. It is advantageous that one ore more human milk oligosaccharides can move from a disposable absorbent article to the skin of a wearer, i.e. the human milk oligosaccharides dissolve in the urine or other exudates. For illustration, when a substrate on which one ore more human milk oligosaccharides are applied is soaked in water (liquid temperature: 25° C.) in an amount of 10 times of the weight of this substrate, all human milk oligosaccharides composition are substantially completely dissolved or dispersed.

When the substrate is either a nonwoven web or a film or a tissue, one or more human milk oligosaccharides which are either selected from lactose, 2'-fucosyllactose, 3'-fucosyllactose, difucosyllactose, lacto-N-tetraose (type 1), lacto-N-neo-tetraose (type 2), lacto-N-fucopentaoses I, II, III, IV and V, lacto-N-fucohexaose I, lacto-N-hexaose, lacto-N-neohexaose, fucosyllacto-N-hexaose I and IV, fucosyllacto-N-neohexaose, lacto-N-difuco-hexaoses I and II, lacto-N-octaoses, sialyα2-3lactose, sialyα2-6lactose, sialyl-lacto-N-tetraose a, b and c, and disialyl-lacto-N-tetraose, and mixtures thereof, or selected from fucose-α(1→2) galalactose_β as a disaccharide unit, 2'-fucosyllactose, 3'-fucosyllactose, lacto-N-difuco-tetraose, lacto-N-difuco-hexose I, lacto-N-difuco-hexose II, lacto-N-fucopentaose I, lacto-N-fucopentaose II, lacto-N-fucopentaose III, and lacto-N-fucopentaose V, or mixtures thereof; may represent at least 50% of the total weight of the human milk oligosaccharides comprised by the substrate.

When the substrate is either a nonwoven web or a film or a tissue, at least a portion of the substrate may be coated or impregnated with one or more human milk oligosaccharides with an amount of 0.2 g to 200 g of all human milk oligosaccharides per square meter, between 5.0 g and 100 g per square meter, between 8.0 g and 50 g per square meter.

Disposable Absorbent Articles

A disposable absorbent article refers to a device which absorbs and retains body exudates and is not intended to be laundered or otherwise restored or reused as an absorbent article after a single use.

When the disposable absorbent article is a diaper, a pant, an adult incontinence product, an absorbent insert for a diaper or pant, a wipe or a feminine hygiene product, such as a sanitary napkin and a panty liner, one or more of the substrates described previously form at least a portion of the disposable absorbent article.

In the following a wipe is described. For instance, the wipe may be made of or may comprise a nonwoven web substrate comprising one or more human milk oligosaccharides as described above.

Whilst not limited to a particular use, the wipe may be intended for cleaning the body, in particular the peri-anal area after defecation and/or the external genital area after urination of babies, toddlers and adults. Other examples of wipes include feminine hygiene wipes.

When the disposable absorbent article is a diaper, a pant, an adult incontinence product, an absorbent insert for a diaper or pant, or a feminine hygiene product, such as a sanitary napkin and a panty liner, this disposable absorbent article typically comprises a liquid pervious topsheet, a liquid impervious backsheet and an absorbent core positioned between the topsheet and the backsheet. One or more of the substrates described previously can form at least a portion of the disposable absorbent article.

The following description generally discusses the absorbent core, topsheet, and backsheet materials that are useful in disposable absorbent articles. It is to be understood that this general description applies to these components of the specific absorbent articles shown in FIG. 1 and further described below, in addition to those of other disposable absorbent articles which are generally described herein.

In general, the absorbent core is capable of absorbing or retaining liquids (e.g., menses, urine, and/or other body exudates). The absorbent core may be compressible, conformable, and non-irritating to the wearer's skin. The absorbent core may be manufactured in a wide variety of sizes and shapes (e.g., rectangular, oval, hourglass, "T" shaped, dog bone, asymmetric, etc.). In addition to the absorbent composites of the present disclosure, the absorbent core may include any of a wide variety of liquid-absorbent materials commonly used in absorbent articles, such as comminuted wood pulp.

The absorbent core can include other absorbent components that are often used in absorbent articles, for example, an acquisition system, or a secondary topsheet for increasing the wearer's comfort. When the disposable absorbent article is a diaper, a pant, an adult incontinence product, an absorbent insert for a diaper or pant, or a feminine hygiene product, such as a sanitary napkin and a panty liner, one or more of the substrates described previously may form at least a portion of the absorbent core and/or the acquisition system.

The backsheet is impervious to liquids (e.g., menses and/or urine) and may comprise a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material.

The topsheet may be compliant, soft feeling, and non-irritating to the wearer's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), including apertured nonwovens; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, spunlace carded, wet-laid, melt-blown, hydroentangled, hydroformed, hydroapertured, combinations of the above, or the like.

One of the substrates described previously may form at least a portion of the topsheet or a portion of a layer directly underneath the topsheet.

One or more human milk oligosaccharides may also be comprised in a formulation which is coated or sprayed onto the topsheet.

The absorbent core may be joined with the topsheet, the backsheet, or both in any manner as is known by attachment means (not shown in FIG. 1) such as those well known in the art. However, embodiments of the present disclosure are envisioned wherein portions or the entire absorbent core are unattached to either the topsheet, the backsheet, or both.

The disposable absorbent article may further comprise barrier leg cuffs for providing improved containment of liquids and other body exudates. The barrier leg cuffs may comprise one or more of the substrates wherein at least a portion of the substrate comprises with one or more human milk oligosaccharides, as described previously.

Diaper

A typical disposable absorbent article comprising the substrate which includes one or more human milk oligosaccharide is represented in FIG. 1 in the form of a diaper 20.

In more details, FIG. 1 is a plan view of an exemplary diaper 20, in a flat-out state, with portions of the structure being cut-away to more clearly show the construction of the diaper 20.

This diaper 20 is shown for illustration purpose only as the disclosure may used for making a wide variety of diapers or other absorbent articles. In the following, the term diaper will be used for convenience, being understood that what follows can be applied to any other type of absorbent articles unless specifically excluded.

As shown in FIG. 1, the absorbent article, here a diaper, can comprise a liquid pervious topsheet 24, a liquid impervious backsheet 26, an absorbent core 28, which may be positioned between at least a portion of the topsheet 24 and the backsheet 26. The absorbent core 28 comprises superabsorbent polymer 60. The diaper 20 may also include optionally an acquisition system with an upper and lower acquisition layer (52 and 54).

One or more of the substrates described previously may also form at least a portion of the absorbent core 28 and/or the acquisition system (52+54).

The diaper may also comprise elasticized leg cuffs 32 and barrier leg cuffs 34, and a fastening system which can comprise adhesive tabs 42 cooperating with a landing zone 44, and other elements, which are not represented, such as a back elastic waist feature and a front elastic waist feature, side panels or a lotion application.

The diaper 20 as shown in FIG. 1 can be notionally divided in a first waist region 36, a second waist region 38 opposed to the first waist region 36 and a crotch region 37 located between the first waist region 36 and the second waist region 38 (the first and second waist regions each corresponding to about 30% of the length of the diaper and the crotch region the remaining 40%). The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper. The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20.

The chassis 22 of the diaper 20 comprises the main body of the diaper 20. The chassis 22 may comprise the absorbent core 28 and an outer covering including the topsheet 24 and/or the backsheet 26. The majority of diapers are unitary, which means that the diapers are formed of separate parts united together to form a coordinated entity so that they do not require separate manipulative parts like a separate holder and/or liner.

The chassis 22 comprises the main structure of the diaper with other features such as back ears 40, front ears 46 and/or barrier cuffs 34 attached to form the composite diaper structure. The topsheet 24, the backsheet 26, and the absorbent core 28 may be assembled in a variety of well known configurations, in particular by gluing or heat embossing. Exemplary diaper configurations are described generally in U.S. Pat. Nos. 3,860,003, 5,221,274, 5,554,145, 5,569,234, 5,580,411, and 6,004,306.

One or more human milk oligosaccharides may also be comprised in a formulation which is coated or sprayed onto the topsheet 24.

The diaper 20 may comprise leg cuffs 32 which provide improved containment of liquids and other body exudates. Leg cuffs 32 may also be referred to as leg bands, side flaps, barrier cuffs, or elastic cuffs. Usually each leg cuffs will comprise one or more elastic string 33, represented in exaggerated form on FIG. 1 comprised in the chassis of the diaper for example between the topsheet and backsheet in the area of the leg openings to provide an effective seal while the diaper is in use. It is also usual for the leg cuffs to comprise "stand-up" elasticized flaps (barrier leg cuffs 34) which improve the containment of the leg regions. The barrier leg cuffs 34 may comprise one of the substrates wherein at least a portion of the substrate comprises one or more human milk oligosaccharides, as described previously.

Of course, it will be recognized that any disposable absorbent article design may be utilized to carry out the methods of the present disclosure, so long as one or more human milk oligosaccharides are applied to one or more substrates that form at least a portion of the disposable absorbent article so as to be transferred to the wearer's skin during use. The disclosure above is merely for illustrative purposes.

In all the cases, the overall amount of all human milk oligosaccharides per disposable absorbent article is comprised between 0.02 g and 0.5 g, or between 0.2 g and 0.4 g.

The efficient amount of microorganisms may be more than 9 CFU (Colon Forming Units) per 0.1 square meter of a substrate. CFU as used herein means Colon Forming Units as determined with the Miles and Misra method (Miles, A A; Misra, S S, Irwin, J O (1938 November), "The estimation of the bactericidal power of the blood", *The Journal of hygiene* 38 (6), 732-49.

Pants

The methods of the present disclosure may also employ training pants to effect delivery of the desired skin care composition. Training pants are disposable garments having fixed sides and leg openings designed for infant or adults wearers. They are placed in position on the wearer by inserting the wearer's legs into the leg openings and sliding the training pant into position about the wearer's lower torso.

Feminine Hygiene Product

In the following, a feminine hygiene product is described (e.g., sanitary napkin or panty-liner). A feminine hygiene product may comprise a topsheet, a backsheet, and an absorbent core positioned between the topsheet and backsheet; each component having a body facing surface and a garment facing surface. The topsheet or a layer underneath the topsheet may be made of a substrate comprising one or more human milk oligosaccharides of the present disclosure as described herein. The backsheet can be any known or otherwise effective backsheet material, provided that the backsheet prevents external leakage of exudates absorbed and contained in the feminine hygiene article.

The feminine hygiene product also comprises an absorbent core. The absorbent core is typically positioned between the topsheet and the backsheet. The size and shape of the absorbent core can be altered to meet absorbent capacity requirements, and to provide comfort to the wearer/user. The absorbent core suitable for use in the present disclosure can be any liquid-absorbent material known in the art for use in absorbent articles, provided that the liquid-absorbent material can be configured or constructed to meet absorbent capacity requirements.

The feminine hygiene product may also comprise wings which may enable attachment to the underwear of the wearer. The wings may be made of, or comprise a substrate comprising one or more human milk oligosaccharides useful in the present disclosure. The sanitary napkins and/or panty-liners herein may comprise a fastening means comprised by the backsheet and/or by the wings. Exemplary adhesive attachment means are present on, or attached to, at least the backsheet.

Process for Manufacturing a Disposable Absorbent Article Comprising a Substrate

In making disposable absorbent articles to carry out the methods of the present disclosure, one or more human milk oligosaccharides are applied such that during wear, at least some portion of the amount of one or more human milk oligosaccharides may transfer from the treated article to the wearer's skin in order to address skin disorders.

One or more human milk oligosaccharides are either applied directly to one or more wearer contacting surfaces, or is applied to alternate locations or means such that one or more human milk oligosaccharides are readily available for transfer from one or more wearer contacting surfaces during use (for example, materials positioned beneath the wearer contacting surface, encapsulated compositions, etc.).

To effectuate delivery of the human milk oligosaccharides to those body regions most susceptible to skin disorders, one or more human milk oligosaccharides may be included on the portion of the topsheet and barrier leg cuffs that will directly contact the wearer's buttocks, genitals, intertriginous and anal regions during wear.

Additionally, one or more human milk oligosaccharides may be applied to other disposable absorbent article regions for delivery to one or more of the wearer's hips, abdomen, back, waist, sides, thighs, etc. It may also be included in a wipe.

Suitable methods for applying an amount of one or more human milk oligosaccharides to the substrate include spraying, printing (e.g., flexographic printing), coating (e.g., contact slot coating, gravure coating), extrusion, microencapsulation or combinations of these application techniques, e.g., spraying one or more human milk oligosaccharides on a rotating surface, such as a calendar roll, that then transfers one or more human milk oligosaccharides to the desired portion of the disposable absorbent article.

One or more human milk oligosaccharides can be applied to the disposable absorbent article at any point during assembly. For example, one or more human milk oligosaccharides can be applied to the finished disposable absorbent article before it is packaged. One or more human milk oligosaccharides can also be applied to a given component (e.g., topsheet, cuffs, sides, waist, etc.), before it is combined with the other components to form a finished disposable absorbent article. Again, one or more human milk oligosaccharides can be applied to other zones of the disposable absorbent article such that one or more human milk oligosaccharides will migrate to one or more wearer contacting surfaces during use.

What is claimed is:

1. A substrate selected from the group consisting of a nonwoven web, a film, a tissue, a pulp, and a superabsorbent polymer, wherein at least a portion of the substrate has added thereto a formulation comprising one or more human milk oligosaccharides, the one or more human milk oligosaccharides comprising a linear or branched chain of carbohydrate units wherein the overall carbohydrate unit number is from 2 to no more than 32, each carbohydrate unit containing 3 to 6 carbon atoms, wherein said carbohydrate units are covalently bound to each other directly or indirectly by an ether function, the substrate and the formulation being adapted to effect transfer of the formulation to a baby's skin.

2. The substrate of claim 1, wherein one or more human milk oligosaccharides are selected from the group consisting of: lactose, 2'-fucosyllactose, 3'-fucosyllactose, difucosyllactose, lacto-N-tetraose (type 1), lacto-N-neo-tetraose (type 2), lacto-N-fucopentaoses I, II, III, IV and V, lacto-N-fucohexaose I, lacto-N-hexaose, lacto-N-neohexaose, fucosyllacto-N-hexaose I and IV, fucosyllacto-N-neohexaose I and II, lacto-N-octaoses, sialyα2-3lactose, sialyα2-6lactose, sialyl-N-tetraose a, b and c, and disialyl-lacto-N-tetraose, and mixtures thereof.

3. The substrate of claims 1, wherein the one or more human milk oligosaccharides are selected from the group consisting of:
fucose-α(1→2)galalactose_βas a disaccharide unit, 2'-fucosyllactose, 3'-fucosyllactose, lacto-N-difuco-tetraose, lacto-N-difuco-hexose I, lacto-N-difuco-hexose II, lacto-N-fucopentaose I, lacto-N-fucopentaose II, lacto-N-fucopentaose III, and lacto-N-fucopentaose V, and mixtures thereof.

4. The substrate of claims 1, wherein the substrate is selected from the group consisting of a nonwoven web, a film, and a tissue wherein one or more human milk oligosaccharides which are either selected from the group consisting of:
lactose, 2'-fucosyllactose, 3'-fucosyllactose, difucosyllactose, lacto-N-tetraose (type 1), lacto-N-neo-tetraose (type 2), lacto-N-fucopentaoses I, II, III, IV and V, lacto-N-fucohexaose I, lacto-N-hexaose, lacto-N-neohexaose, fucosyllacto-N-hexaose I and IV, fucosyllacto-N-neohexaose, lacto-N-difuco-hexaoses I and II, lacto-N-octaoses, sialyα2-3lactose, sialyα2-6lactose, sialyl-lacto-N-tetraose a, b and c, and disialyl-lacto-N-tetraose, and mixtures thereof, or selected from the group consisting of:
fucose-α(1→2)galalactose_βas a disaccharide unit, 2'-fucosyllactose, 3'-fucosyllactose, lacto-N-difuco-tetraose, lacto-N-difuco-hexose I, lacto-N-difuco-hexose II, lacto-N-fucopentaose I, lacto-N-fucopentaose II, lacto-N-fucopentaose III, and lacto-N-fucopentaose V, and mixtures thereof;
represent at least about 50% of the total weight of all the human milk oligosaccharides comprised by the substrate.

5. The substrate of claim 1, wherein the human milk oligosaccharides are comprised in a formulation, wherein formulations include emulsions, creams, ointments, salves, powders, suspensions, solutions, encapsulations, gels and combinations thereof.

6. The substrate of claim 5, wherein the formulation includes an immobilizing agent.

7. The substrate of claim 1, wherein the substrate is selected from the group consisting of a nonwoven web, a film, and a tissue and wherein at least a portion of the substrate is coated or impregnated with one or more human milk oligosaccharides with an amount of about 0.2 g to about 200 g of all human milk oligosaccharides per square meter.

8. A wipe wherein one or more substrates according to claim 1 form at least a portion of the wipe.

9. A disposable absorbent article comprising the substrate of claim 1, wherein the disposable absorbent article is selected from the group consisting of a diaper, a pant, an adult incontinence product, an absorbent insert for a diaper or pant, and a feminine hygiene product, wherein the disposable absorbent article comprises a backsheet, a topsheet, and an absorbent core disposed between the backsheet and the topsheet.

10. The disposable absorbent article of claim 9, wherein the substrate forms at least a portion of the topsheet or a portion of a layer directly underneath the topsheet.

11. The disposable absorbent article of the claim 5, wherein the formulation is coated or sprayed onto the topsheet.

12. The disposable absorbent article of claim 9 further comprising barrier leg cuffs, wherein the barrier leg cuffs comprise the substrate.

13. The disposable absorbent article of claim 9 further comprising an acquisition system, wherein the absorbent core or the acquisition system comprises the substrate.

14. The disposable absorbent article of claims 8, wherein the overall amount of all human milk oligosaccharides per disposable absorbent article is between about 0.02 g and about 0.5 g.

15. A process for manufacturing a disposable absorbent article comprising the substrate of claim 1, the process comprising the step of applying an amount of one or more human milk oligosaccharides to the substrate.

16. The process of claim 15, wherein the human milk oligosaccharides are applied to the substrate via spraying, printing, coating, slot coating, extrusion, microencapsulation and any combination thereof.

* * * * *